United States Patent [19]

Holland

[11] Patent Number: 4,651,726
[45] Date of Patent: Mar. 24, 1987

[54] ANKLE BRACE

[76] Inventor: Michael H. Holland, 23890 Coach House Rd., Southfield, Mich. 48075

[21] Appl. No.: 776,841

[22] Filed: Sep. 17, 1985

[51] Int. Cl.⁴ .......................... A61F 13/06; A61F 5/00
[52] U.S. Cl. .................................. 128/166; 128/166.5; 128/80 H
[58] Field of Search .................. 128/166, 166.5, 80 H, 128/89 R, 90, 83.5; 36/89

[56] References Cited

U.S. PATENT DOCUMENTS

| | | | |
|---|---|---|---|
| 1,205,206 | 11/1916 | Hofmeister | 36/89 |
| 1,441,677 | 1/1923 | Golden | 36/89 |
| 1,692,896 | 11/1928 | Hilgert | 36/107 |
| 3,298,365 | 1/1967 | Lewis | 128/80 H |
| 3,970,083 | 7/1976 | Carrigan | 128/166 |
| 4,280,488 | 7/1981 | Polsky et al. | 128/166 X |
| 4,420,895 | 12/1983 | Baumann et al. | 36/118 |
| 4,454,871 | 6/1984 | Mann et al. | 128/80 |

FOREIGN PATENT DOCUMENTS 0508227 10/1920 France .............................. 128/80 C Primary Examiner—Richard J. Johnson
Assistant Examiner—Kathleen J. D'Arrigo
Attorney, Agent, or Firm—Olson & Hierl

[57] ABSTRACT

An ankle brace includes a flexible jacket into which the foot and ankle to be braced can be inserted with an L-shaped support means removably affixed to a lateral surface of the jacket. The support means comprises two separate, elongated members insertable into an L-shaped pocket formed on the jacket. Ends of the two elongated members overlap. If the foot attempts to roll under the ankle, the rotational motion is transferred from the lower, generally horizontal elongated member to the upper, generally vertical elongated member. The upper elongated member and the jacket cooperate with the lower elongated member to inhibit rotation of the lower member thereby blocking rotation of the foot under the ankle.

13 Claims, 5 Drawing Figures

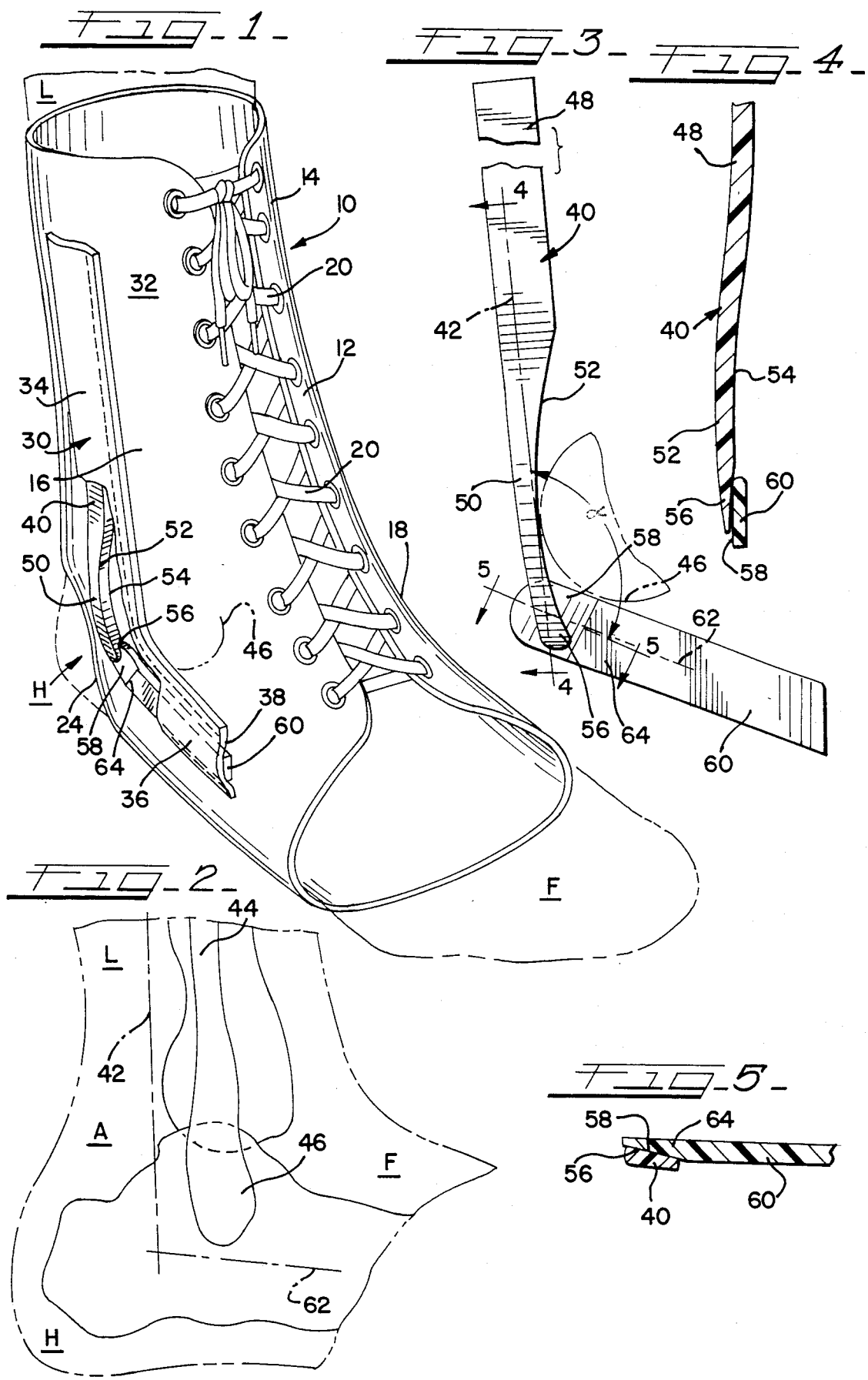

ANKLE BRACE

TECHNICAL FIELD

The present invention relates to an ankle brace that limits the torsional motion of the ankle, relative to the foot whereby the tissues and ligaments of the ankle and foot are protected from injury or reinjury due to unrestricted motion. At the same time, the normal walking movement of the ankle relative to the foot is not limited.

BACKGROUND OF THE INVENTION

Sprained ankles are a relatively common form of athletic injury. In normal walking, the foot moves relative to the ankle without straining or damaging tissues and ligaments. Generally, when an ankle is sprained, the tissues and ligaments on the lateral (or outer) side of the ankle are stretched or torn, for example, as the foot rolls under the ankle in an undesirable motion.

Various attempts have been made to provide ankle braces which support the lateral side of the ankle and restrict the torsional motion of an injured ankle relative to the foot. These braces also attempt to permit a normal walking motion.

U.S. Pat. No. 1,441,677 to Golden entitled "Braced Shoe" discloses a shoe that includes a lateral side brace. The brace includes three elongated members that are pivotably attached to one another by a rivet so as to form a generally T-shaped structure. One member of the T extends generally vertically between the top and bottom of the shoe. Another member of the T extends generally horizontally from a central region of the vertical member. The brace is fixedly attached to the shoe.

U.S. Pat. No. 3,970,083 to Carrigan entitled "Ankle Support" discloses a flexible jacket that also includes a T-shaped brace. The brace has a generally horizontal member which extends over the lateral malleolus of the fibula, and a generally vertical member that intersects the horizontal bracing member over the lateral malleolus. The brace does not appear to be removable from the flexible jacket.

U.S. Pat. No. 4,280,488 to Polsky et al. entitled "Ankle Support With Elastic Panel" discloses a flexible jacket into which an ankle and foot can be inserted. Removable, elongated stays may be inserted into pockets on the lateral and medial side of the jacket. The stays of Polsky et al. are elongated straight members.

U.S. Pat. No. 4,454,871 to Mann et al. entitled "Ankle-Foot Orthosis" discloses an ankle and foot brace which includes integrally formed L-shaped bracing members. The L-shaped members are formed on the lateral and the medial sides of the brace, and they cannot be removed from the brace.

Despite the development of the braces of the prior art, there continues to be need for an effective brace which can be readily fitted about an injured foot and ankle, and which prevents further injury thereto. This brace should permit normal walking motion of the foot relative to the ankle but should restrict any undesirable motion thereof. The motions to be restricted include the rolling of the foot under the ankle with the attendant stretching and damaging of tissues and ligaments on the lateral side of the ankle.

This brace should also be lightweight and easy to use. Further, it should be inexpensive and usable without special training or equipment.

SUMMARY OF THE INVENTION

In accordance with the invention, an ankle brace is provided for flexibly restraining an ankle and foot in a selected relationship. An ankle brace embodying the invention includes a flexible jacket which can be positioned on the ankle and foot to be braced. An L-shaped support means can be affixed to a lateral surface of the jacket. Cooperation between the jacket and the support means prevents injury or reinjury of tissues and ligaments resulting from undesirable movement of the ankle relative to the foot.

The L-shaped support means can include first and second elongated members for restraining improper movement of the ankle. The first and second elongated members can be removably affixed to the lateral surface of the jacket. In one particular form of the invention, the first and second elongated members can comprise rigid lengths of a plastic material.

The first and second elongated members are positioned, with ends adjacent one another, generally in the shape of an "L." The first elongated member is oriented generally along the fibula with a lower portion positioned adjacent a posterior side of the lateral malleolus of the fibula. The second elongated means is oriented generally along the foot with a proximal end positioned below the lateral malleolus. The lower portion of the first elongated member is in sliding contact with the proximal end of the second elongated member.

In a particular ankle brace embodying the invention, the sliding contact is achieved by overlapping the respective ends of the two rigid elongated members without connecting those members together. The rigid elongated members can be removably attached to the lateral surface of the jacket. The jacket can include an L-shaped pocket into which the rigid elongated members can be inserted in overlapping relationship.

The lateral malleolus is generally in the shape of a hemisphere that extends outwardly from the lateral surface of the ankle. In order to closely position the first elongated member adjacent the lateral malleolus, the first elongated member can be curved in first and second directions.

In particular, the lower section of the first elongated member can include a first curved surface positionable adjacent the lateral malleolus. The lower section can also be curved in a second direction so as to conform to the outwardly extending, lower portion, of the lateral malleolus.

Cooperation between the first and second elongated members, and the jacket, substantially restrains torsional movement of the foot relative to the ankle. As a result, further damage to the tissues and ligaments on the lateral side of the ankle is reduced.

The invention also includes a method of restraining a foot from moving improperly relative to an ankle that includes the steps of:

providing first and second elongated members;

positioning the first elongated member generally vertically with a lower end adjacent a posterior surface of the lateral malleolus of the ankle;

positioning the second elongated member generally horizontally along the lateral surface of the foot, below the lateral malleolus, with a proximal end in sliding contact with the lower end of the first elongated member;

transferring forces generated as the ankle tends to improperly move, relative to the foot, to the proximal end of the second elongated member; and opposing the forces transferred along the second elongated member with the first elongated member thereby restraining the ankle.

Numerous other advantages and features of the present invention will become readily apparent from the following detailed description of the invention and the embodiments thereof, from the claims and from the accompanying drawings in which the details of the invention are more fully and completely disclosed as a part of this specification.

BRIEF DESCRIPTION OF THE DRAWING

FIG. 1 is a perspective view of an ankle brace embodying the present invention with portions partly broken away and showing, in phantom, an ankle and foot being braced;

FIG. 2 is a simplified, fragmentary, side schematic view showing the relationships of the rigid elongated members of the ankle brace of FIG. 1 to portions of the foot and ankle of FIG. 1;

FIG. 3 is a side view illustrating the relationship of the rigid elongated members to the lateral malleolus of the fibula of the foot shown in FIG. 2;

FIG. 4 is a sectional view taken along a plane identified by line 4—4 of FIG. 3; and FIG. 5 is a fragmentary view in section taken along a plane identified by line 5—5 of FIG. 3.

DETAILED DESCRIPTION OF A PREFERRED EMBODIMENT

While this invention is susceptible of embodiment in many different forms, a specific embodiment is shown in the drawing and is described herein. It will be understood, however, that the present disclosure is only an example of the principles of the invention and is not intended to limit the invention to the specific embodiment illustrated and described.

Referring to FIG. 1, an ankle brace 10 in accordance with the present invention is positioned on a leg L, ankle A and foot F to be supported or braced. The brace 10 includes a flexible support jacket 12 with an upper region 14 which is positioned adjacent a part of the leg L, and a lateral surface 16 which is positioned adjacent a lateral surface of the ankle A. A lower region 18 of the jacket 12 surrounds a portion of the foot F which is being braced.

The jacket 12 can be formed of a flexible material, such as leather or a plastic. The particular material used to form the jacket 12 is not a limitation of the present invention. Leather is particularly advantageous, however, since it is a natural material that will breathe and will allow some maintenance of body heat as a therapeutic agent which promotes the healing process.

The jacket 12 can be adjustably positioned around the leg L, ankle A and foot F by means of laces 20. The fit of the jacket 12 can be improved by a cutout 24 in the region of the heel H.

An advantage of the ankle brace 10 is that the jacket 12 is designed so as to permit normal walking motion of the ankle relative to the foot F.

An L-shaped pocket 30 is affixed by stitches 32 or the like to the lateral surface 16 of the jacket 12. The pocket 30 has an upper region 34 which is oriented generally vertically when the jacket 12 is properly placed on the ankle A and foot F. The pocket 30 has a lower region 36 which is oriented generally horizontally when the jacket 12 is positioned on the ankle A. The pocket regions 34 and 36 define an L-shaped opening 38 along the lateral surface 16.

A first or upper rigid elongated member 40 is insertable into the upper region 34 of the L-shaped pocket 30. As can best be seen in FIG. 2, the first elongated member 40 has a center line 42 which is oriented so as to be generally vertical and co-extensive with the fibula 44 of the ankle A. The fibula 44 terminates in the lateral malleolus 46. The lateral malleolus 46 appears as a generally hemispherical protrusion on the lateral surface of the ankle. The center line 42 of the first elongated member 40 is positioned adjacent a posterior side of the lateral malleolus 46.

The first elongated member 40 has an upper region 48 and a lower region 50. The upper region 48 extends upwardly toward the top region 14 of the jacket 12. The lower region 50 is positioned adjacent the posterior side of the lateral malleolus 46.

The lower region 50 includes an arcuate surface 52 which provides for positioning the lower region 50 adjacent the generally, hemispherical lateral malleolus 46.

The lower region 50 is also formed with a curved surface 54, as can be best seen in FIG. 4, which is positioned adjacent the lower portion of the lateral malleolus. The curved surface 54 permits the lower region of the first rigid elongated member 40 to be positioned directly against the curved surface of the ankle A which is co-extensive with the center line 42 of the first elongated member 40.

The lower region 50 terminates in a beveled or sloped surface 56. The function and operation of the beveled surface 56 is discussed below.

A second or lower rigid elongated member 60 is insertable into the lower region 36 of the L-shaped pocket 30. The second elongated member 60 has a center line 62, which, as can best be seen in FIG. 2, is positioned so as to pass beneath the lateral malleolus 46. The second elongated member 60 has a proximal end 64 having a beveled or sloped surface 58 which slidably and rotatably engages the beveled surface 56 of the lower region 50 of the first elongated member 40. This interaction can best be seen in FIGS. 3-5.

Referring to FIG. 3, in a preferred mode of practicing the invention, the center lines 42 and 62 of the elongated members 40 and 60, respectively, cross at an angle (alpha) of about 120 degrees.

The slidable interaction between the elongated members 40 and 60 permits the ankle A to move normally with respect to the foot F with little or no interference. However, in the event that the foot F attempts to roll or twist under the ankle A as frequently is the case with strained or twisted ankles, the rotational motion of the second elongated member 60 is translated to the proximal end 64 thereof. As the proximal end 64 attempts to rotate, it engages the beveled surface 56 of the first elongated member 40. The upper 34 region of the pocket 30 restrains or holds the first elongated member 40 against the lateral surface 16 of the jacket 12. The rotational motion of the proximal end 64 is thus opposed and blocked by the beveled surface 56. Hence, cooperative interaction between the jacket 12 and the first and second elongated members 40 and 60 substantially restrains undesired motion of the ankle relative to the foot.

The members 40 and 60 can be formed of any lightweight rigid material which is strong enough to withstand the rotational forces generated by the movement of the ankle relative to the foot. The particular material of which the members 40 and 60 is formed, however, is not a limitation of the present invention.

From the foregoing, it will be observed that numerous variations and modifications may be effected without departing from the true spirit and scope of the novel concepts of the invention. It is to be understood that no limitation with respect to the specific apparatus illustrated herein is intended or should be inferred. It is, of course, intended to cover by the appended claims all such modifications as fall within the scope of the claims.

What is claimed is:

1. An ankle brace for flexibly restraining an ankle and foot in a selected relationship comprising:
   a flexible jacket, with an upper section and a lower section, for surrounding portions of the ankle and foot; and
   first and second elongated members for restraining undesired movement of the ankle relative to the foot;
   said first elongated member being removably affixed to a lateral surface of said jacket, oriented with a lower region including a tapered surface positionable adjacent a posterior portion of the lateral malleolus of the fibula of the ankle, with an upper region extending therefrom toward said upper region of said jacket, and said second elongated member being removably affixed to said lateral surface of said jacket oriented with a proximal end including a tapered surface positionable adjacent a lower portion of the lateral malleolus of the fibula of the ankle, in rotatable and slidable contact with the lower region of said first elongated member, said tapered surfaces being positioned in an overlapping relationship;
   said jacket, said first elongated member and said second elongated member cooperating to substantially restrain the ankle from undesired movement relative to the foot without restraining normal walking motion.

2. The ankle brace according to claim 1 wherein said first elongated member is rigid with said lower region thereof including an arcuate surface locatable adjacent the lateral malleolus.

3. The ankle brace according to claim 2 wherein said lower region of said first elongated member is curved in correspondence with an adjacent outwardly curved portion of the lateral malleolus.

4. The ankle brace according to claim 2 wherein said second elongated member is rigid with the proximal end thereof in sliding contact with said lower region of said first elongated member.

5. The ankle brace according to claim 4 wherein the jacket includes a generally L-shaped pocket on said lateral surface with said first and second elongated members positioned therein.

6. The ankle brace according to claim 5 wherein said first and second elongated members are in a separable, overlapping, slidable, and rotatable relationship.

7. An ankle brace comprising:
   a flexible jacket removably fittable about a foot and ankle to be braced including a lateral side portion and a medial side portion; and
   L-shaped support means removably affixed to said lateral side portion, for restraining the ankle from undesirable movement relative to the foot, said L-shaped support means including first and second rigid elongated members with said first elongated member generally oriented in a first direction with a lower region including a sloped surface adjacent the posterior side of the lateral malleolus of the fibula and with said second elongated member generally oriented along a second direction with a proximal end including a tapered surface and positioned below the lateral malleolus of the fibula, said sloped surfaces being positioned in overlapping relationship whereby said second elongated member is in slidable contact with said first elongated member.

8. The ankle brace according to claim 7 wherein said lower region of said first elongated member includes a curved surface positionable adjacent the lateral malleolus.

9. The ankle brace according to claim 7 wherein said lower region is curved in accordance with an outwardly curved posterior section of the lateral malleolus.

10. The ankle brace according to claim 8 wherein the lateral side portion of said jacket includes an L-shaped pocket and said first and second elongated members are slidably received by the L-shaped pocket.

11. The ankle brace according to claim 7 wherein said jacket comprises a single member that surrounds the sides and lower surface of the foot.

12. A method of restraining an ankle from undesired movement relative to a foot comprising:
   providing first and second elongated members;
   positioning the first elongated member generally vertically with a lower end including a tapered surface adjacent a posterior surface of the lateral malleolus of the ankle;
   positioning the second elongated member generally horizontally, below the lateral malleolus, with a proximal end including a tapered surface in sliding contact with the tapered surface of the lower end of the first elongated member;
   transferring forces generated as the ankle tends to undesirably move relative to the foot to the proximal end of the second elongated member; and
   opposing the forces, transferred to the proximal end of the second elongated member, with the first elongated member thereby restraining the tendency of the ankle to move undesirably with respect to the foot.

13. The method according to claim 12 including positioning the tapered surfaces of the first and second elongated members in overlapping relationship.

* * * * *